United States Patent [19]
Joyce

[11] Patent Number: 5,517,427
[45] Date of Patent: May 14, 1996

[54] ON-SITE OIL ANALYZER

[75] Inventor: Carlton S. Joyce, Atlanta, Ga.

[73] Assignee: On-Site Analysis, Inc., Atlanta, Ga.

[21] Appl. No.: 254,039

[22] Filed: Jun. 3, 1994

Related U.S. Application Data

[62] Division of Ser. No. 220,274, Mar. 30, 1994.

[51] Int. Cl.⁶ .......................... G06G 7/57; G05B 23/02; G01N 33/26; G01N 21/00
[52] U.S. Cl. .......................... 364/510; 364/498; 340/631; 340/825.06; 340/825.15; 73/53.05; 73/61.41; 73/61.48; 73/61.71; 73/863.11; 356/70; 356/72; 356/73; 250/301; 250/339.12
[58] Field of Search .......................... 364/509, 510, 364/496, 497, 498, 499; 340/631, 19.11, 825.06, 825.07, 825.15; 73/53.01, 53.05, 53.07, 61.41, 61.42, 61.43, 61.44, 61.48, 61.71, 863.11; 356/70, 72, 73; 250/301, 339.12

[56] References Cited

U.S. PATENT DOCUMENTS

| | | | |
|---|---|---|---|
| 3,526,127 | 9/1970 | Sarkis | 73/53.05 |
| 4,055,986 | 11/1977 | Stewart et al. | 73/61.71 |
| 4,573,115 | 2/1986 | Halgrimson | 340/825.06 |
| 4,833,622 | 5/1989 | Barto et al. | 364/509 |
| 4,838,098 | 6/1989 | Barney | 73/61.41 |
| 4,866,594 | 9/1989 | David et al. | 340/825.06 |
| 4,935,875 | 6/1990 | Shah et al. | 364/497 |
| 5,220,517 | 6/1993 | Sierk et al. | 340/825.06 |
| 5,270,945 | 12/1993 | Heath et al. | 364/497 |
| 5,296,911 | 3/1994 | Weyrauch et al. | 356/73 |
| 5,351,118 | 9/1994 | Spinell | 356/72 |
| 5,369,484 | 11/1994 | Haugen | 364/498 |

Primary Examiner—Emanuel T. Voeltz
Assistant Examiner—Eric W. Stamber
Attorney, Agent, or Firm—Howard & Howard

[57] ABSTRACT

The on-site analyzer (10) includes a housing (14). The housing (14) contains an infrared spectrometer (18) and an optical emission spectrometer (24) for testing a sample (12) of oil. A conduit (32) by operation of a pump (40) draws the sample (12) into the conduit (32), and controllably moves the sample (12) to an infrared spectrometer (18) for testing, and subsequently to an optical emission spectrometer (24) for testing. The pump (40) and spectrometers (18, 24) are controlled by a computer (50) for complete automation of testing. The computer (50) performs analysis and diagnosis of the test results from the spectrometers (18, 24) based on sets of known and standard information. The computer (50) may communicate with a central, remote computer (70). Remote computer (70) accumulates results from a plurality of on-site analyzers (10) to obtain trend and wear evaluations, and to update the standard information in each of the on-site analyzers (10).

16 Claims, 8 Drawing Sheets

EVENT TABLE

| EVENT START | EVENT MESSAGE | EVENT |
|---|---|---|
| 10 | Start Pump at 2200 rpm | run /N2 c://setpump.pif 2200 |
| 20 | Stop Pump | run /N2 c://setpump.pif 0 |
| 25 | Run IR Analysis | run /N7 Calcs 2, c://inspec//, 2, c://omnic//baseline.spa |
| 145 | Spark the sample | run /N2 c://station//bin//analysis.pif |
| 200 | Run Pump for 10 seconds at 1000 rpm | run /N2 c://setpump.pif 1000 |
| 210 | Stop the Pump at 0 rpm | run /N2 setpump.pif 0 |
| 212 | Run Pump in Reverse 10 secs at -2200 rpm | run /N2 setpump.pif -2200 |
| 222 | Stop pump 1 rpm | run /N2 setpump.pif 0 |

Fig. 5b

RULE BASE TABLE

| RULE BASE ID | RULE BASE DESCRIPTION |
|---|---|
| OSAD-R | Rule base for diagnosis at a refinery |
| OSAD-U | Standard used oil diagnosis |
| OSAD-UAZ | Special used oil diagnosis (to accomodate unusual Arizona climate) |
| OSAD-I | Standard industrial diagnosis |
| OSAD-I57 | Special industrial diagnosis (to accomodate an unusual customer) |
| QCFTIR | Standard FTIR output bumping |
| QCMETAL | Standard wear metal bumping |
| QC-157 | Special data checking (to accomodate an unusual customer) |

Fig. 5c

RULE DEFINITION TABLE

| RULE ID | RULE EXPRESSION | COMMENTS |
| --- | --- | --- |
| DS_FUEL_S | RR("DS") .and. val(samp_osa-> FUEL) >=10.0 | severe fuel - diesel engine |
| GS_FUEL_S | RR("GS") .and. val(samp_osa-> FUEL) >=8.5 | severe fuel - gasoline engine |
| PB_MAC_A | RR("MACK") .and. val(samp_osa->PB) >=40 .and. val(samp_osa->PB) >100 | abnormal lead - Mack engine |
| PB_MAC_S | RR("MACK") .and. val(samp_osa->PB) >=100 | severe lead - Mack engine |
| DS | samp_osa->SYSTEM="DS" | Is sample from diesel engine? |
| GS | samp_osa->SYSTEM="GS" | Is sample from gasoline engine? |
| MACK | samp_osa->MAKE="MACK" | Is sample from a Mack engine? |
| GS_RINGS | samp_osa->CG_FUEL + samp_osa->CG_GLY = "SN" | fuel is severe, glycol is normal, motor is gasoline thus bad rings |
| QC_AL_OK | val(samp_osa->AL) > 0 .and. val(samp_osa->AL) <=200 | Data QC on AL ok |
| QC_B_MACK | RR("MACK") .and. val (samp_osa->B) >1000 | Boron too high for Mack vehicle, needs adjustment |
| H2O_DEFLT | val(samp_osa->H2O) <0.1 | low H2O condition |
| FUEL_DEFLT | val(samp_osa->FUEL) <2 | low FUEL condition |

Fig. 5d
RULE CALL TABLE

| RULE BASE ID | SEQ # | RULE ID | ACTION | COMMENT |
|---|---|---|---|---|
| OSAD-U | 1 | DS_FUEL_S | CREPLACE ("samp_osa", "", "CG_FUEL", "S", "O", .f.) | mark fuel condition as severe |
| OSAD-U | 1 | DS_FUEL_S | CREPLACE ("samp_osa", "", "DIAGCODES", "F1", "C", .f.) | add high fuel code in DS to diag codes |
| OSAD-U | 1 | GS_FUEL_S | CREPLACE ("samp_osa", "", "CG_FUEL", "S", "O", .f.) | mark fuel condition as severe |
| OSAD-U | 1 | GS_FUEL_S | CREPLACE ("samp_osa", "", "DIAGCODES", "F2", "C", .f.) | add high fuel code in GS in diag codes |
| OSAD-U | 2 | PB_MAC_A | CREPLACE ("samp_osa", "", "CG_PB", "A", "O", .f.) | mark lead as abnormal |
| OSAD-U | 2 | PB_MAC_A | CREPLACE ("samp_osa", "", "DIAGCODES", "PB", "C", .f.) | make lead remark in diagnosis |
| OSAD-U | 2 | PB_MAC_S | CREPLACE ("samp_osa", "", "CG_FUEL", "S", "O", .f.) | mark lead as severe |
| OSAD-U | 3 | GS_RINGS | CREPLACE ("samp_osa", "", "DIAGCODES", "RR", "C", .f.) | make bad rings remark in diagnosis |
| QCMETAL | 1 | QC_AL_HI | CREPLACE ("samp_osa", "", "AL", ltrim(str(val(samp_osa->AL)*0.88, 5, 2)), "O", .f.) | AL in this case is too high, reduce to 88% of measured value |
| QCMETAL | 1 | QC_B_MACK | CREPLACE ("samp_osa", "", "B", ltrim(str(val (samp_osa->B) +235/2,5,2)), "O", .f.) | Boron in this case is too high for a Mack, average with factory spec of 235 |
| QCFTIR | 1 | H2O_DEFLT | CREPLACE ("samp_osa", "", "FUEL", "LOW", "O", .f.) | low H2O reports simply as "LOW" |
| QCFTIR | 1 | FUEL_DEFLT | CREPLACE ("samp_osa", "", "FUEL", "LOW", "O", .f.) | low FUEL reports simply as "LOW" |

ON-SITE OIL ANALYZER

This is a divisional of copending application Ser. No. 08/220,274 filed on Mar. 30, 1994.

TECHNICAL FIELD

The invention relates to the analysis of an oil sample to determine metal additive content and other organic content, and more particularly, to a self-contained analyzer for on-site use and analysis.

BACKGROUND OF THE INVENTION

Oil is generally utilized to lubricate moving parts in mechanical systems, such as engines, transmissions, and hydraulics in vehicles. Contaminants are not originally present in the oil but are by-products of wear and corrosion in these systems. Metal particulates are formed through abrasion or chemical corrosion and cause further deterioration of internal parts. Normal operation causes oxidation, nitration, and sulfation, but the introduction of additional elements or compounds into the oil accelerates the accumulation of metal particles from abrasion and corrosion. The lubricant filters are designed to remove larger size particulates from oil. However, this leaves the majority of smaller contaminants free to further affect the equipment, especially the nonmetallic components such as pump diaphrams, gaskets and seals, fluid lines, etc.

Concentrations of water in oil affect systems differently, i.e., some systems are of little concern unless above a certain concentration while other systems may be effected with the slightest trace of water. Small amounts of water come from primarily water vapor in the atmosphere, and larger amounts may be due to water leaks, which could damage equipment.

Ethylene glycol is the main component used in anti-freeze products. A significant leak could also damage equipment. Thus, contaminants in oil such as ethylene glycol, fuel, silicon, and soot and other chemicals are also concerns.

Oil analysis provides a method of monitoring wear trends on moving parts of virtually any system or mechanical device. This allows identifying changes from normal wear patterns and thereby predicts progressive damage-type failures. The composition of foreign materials in oil can be determined by a variety of techniques, such as infrared spectrometry, optical emission spectrometry, x-ray fluorescence, etc.

Accurate oil analysis has been provided mainly in a laboratory setting. A system utilized in a laboratory is disclosed in U.S. Pat. No. 3,526,127, issued to Sarkis on Sep. 1, 1970. Sarkis is a semi-automated oil analysis system for a laboratory which utilizes a metal content testing device, a viscometer and an infrared absorbing device. These testing devices transmit their results to a computer which stores reference limits, compares the tested values to the reference limits, and provides evaluation, reporting and trending of oil for various types of engines. An oil sample is separated into three different containers; one container of oil is read by the metal electrometer to determine the concentration of metals; a second container of oil is measured by the viscometer; and a third container of oil is measured by the infrared analyzer to determine contents of water and glycol, and determine oil degradation. The results are sent to a computer which stores the reference information of viscosity, metal content, and infrared characteristics.

It is desirable to have a shop-level or on-site machine that can comprehensively evaluate the condition of an engine, transmission, gear box, or other oil source through the measurement of microscopic wear debris and dissolved contaminants in the equipment's lubricating oil.

SUMMARY OF THE INVENTION

The invention includes an oil analysis system for analyzing the contents of oil. The system comprises a plurality of isolated and remote oil test assemblies each including an oil spectrometer for automatically testing contents of the oil and for storage of test results from the oil spectrometer with associated identification information of the oil. A plurality of communicators transfer the test results with the associated identification information from the plurality of oil test assemblies. A centralized computer assembly is connected to each of the communicators for receiving the test results with the associated identification information and for evaluating the test results based on the identification information to determine characteristics of the test results from a plurality of the remote oil test assemblies.

BRIEF DESCRIPTION OF THE DRAWINGS

Other advantages of the present invention will be readily appreciated as the same becomes better understood by reference to the following detailed description when considered in connection with the accompanying drawings wherein:

FIG. 5a is a table of events stored in the event table memory of the computer controller and FIGS. 5b and 5d are tables of rules stored in the rules memory of the computer controller.

DESCRIPTION OF THE PREFERRED EMBODIMENT

Figure 1:
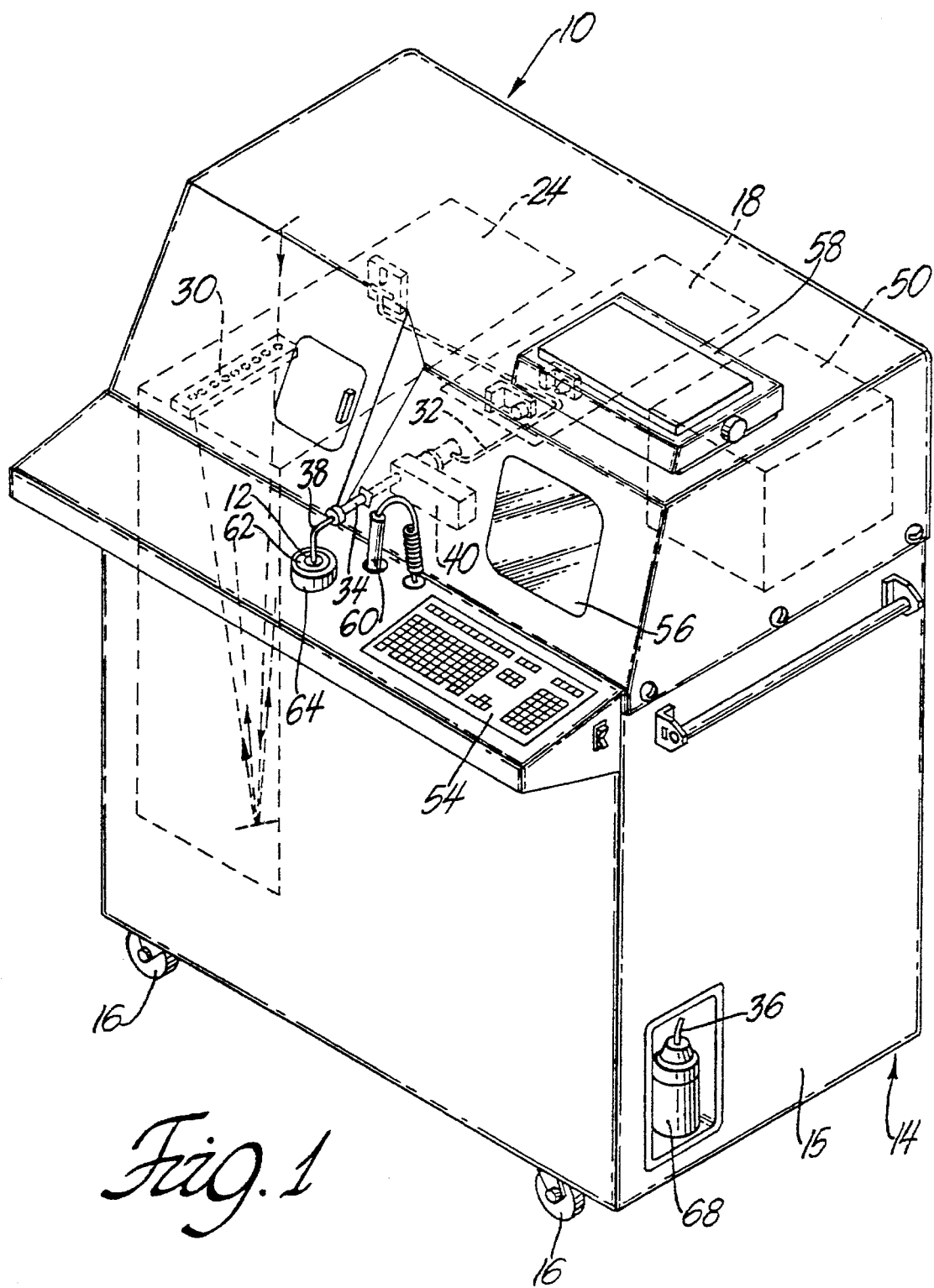
FIG. 1 is a perspective view of the test assembly with internal components indicated in phantom lines.

A test assembly 10 for testing a sample 12 of oil to determine additives and contents thereof is generally illustrated in FIG. 1. The test assembly 10 allows a sample of oil to be tested to determine wear from analysis of contaminants, additive elements, oxidation, nitration, etc., as subsequently discussed. The test assembly 10 automatically performs non-destructive and destructive testing of the sample, analysis and data evaluation, and diagnoses and reports the results and remedial action required based on the analyzed sample 12.

Figure 2:
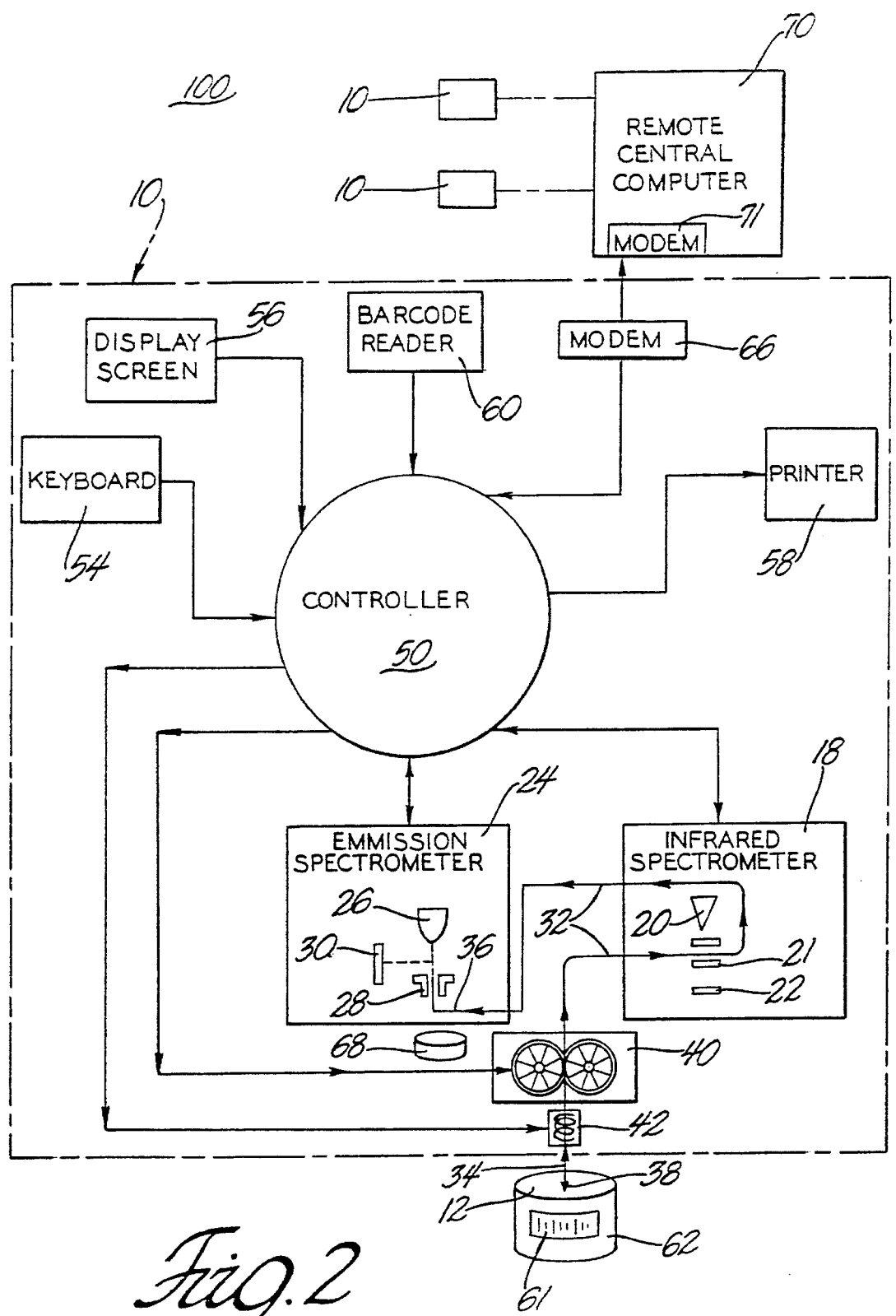
FIG. 2 is a schematic diagram of the analysis system.

As illustrated in FIG. 2, the test assembly 10 is optionally part of an oil analyzing system 100 which includes and incorporates information from a plurality of test assemblies 10 for trend reporting and general data base information and update. The test assembly 10 may operate independent and separate from the remainder of the oil analyzing system 100. The system 100 is subsequently discussed.

The test assembly 10 includes a housing 14 for containing the test equipment to automatically test the sample 12. The housing 14 is generally comprised of a rectangular rigid, supporting structure 15 having wheels 16 attached thereto for allowing mobility of the housing 14 and therefore test assembly 10. The housing 14 provides a self-contained analysis assembly 10.

The test assembly 10 includes an infrared spectrometer 18 within the housing 14 for optically testing the sample 12 and producing first test results. The infrared spectrometer 18 generally provides for testing organic materials in the sample 12, such as oxidation, nitration, sulfation, fuel, water, glycol and soot. The infrared spectrometer 18 is generally known in the art, such as that provided by Thermo Nicholet. The infrared spectrometer 18 produces a spectrograph of the sample 12 indicative of light absorption by the sample 12 at different frequencies, as generally known in the art. Empirical correlations translate the wave peak information to physical parameter values.

The infrared spectrometer 18 generally includes an infrared source 20 for generating a plurality of wave lengths which pass through the sample 12 contained in a flow cell 21, and to a detector 22 which detects absorption of the wave lengths. The infrared spectrometer 18 produces data in the form of peak values from the generated spectrum.

The test assembly 10 also includes an optical emission spectrometer 24 for receiving the sample 12 from the infrared spectrometer 18 and for destructively testing the sample 12 to produce second test results. The optical emission spectrometer 24 generally tests for and measures wear, contaminants, and additive elements found in oil samples 12, such as metals and sand. Optical emission spectrometers 24 are commonly known in the art and are available from Thermo Jarrell Ash. The emission spectrometer 24 produces raw data or test results in "parts per million".

The optical emission spectrometer 24 physically breaks down the fluid sample between and produces a report on the amount of certain metals in the sample 12 based on the optical emissions occurring during breakdown. The optical emission spectrometer 24 generally includes a source electrode 26 and a sample platform electrode 28 for electrical excitation therebetween. Photocells 30 optically monitor the excitation to determine additives based on the produced light spectrum.

The sample 12 of oil is communicated in series through the infrared spectrometer 18 and then through the optical emission spectrometer 24. A channeling means or channelling assembly 32 communicates the sample 12 to the flow cell 21 of the infrared spectrometer 18 and thereafter to the optical emission spectrometer 24. The channelling means 32 generally includes a conduit which includes a first end 34 for receiving the sample 12 of oil to transfer the oil into the conduit 32, and a second end 36 for disposing of the sample of oil 12. The first end 34 of the conduit 32 includes a nozzle 38 connected thereto for submerging within the sample 12 of oil to draw the sample 12 into the conduit 32. The flow cell 21 is connected within the conduit 32 to allow testing by the infrared spectrometer 18.

Also included is pump means 40 operatively connected to the conduit 32 for drawing the sample 12 into the first end 34 and for transferring the sample 12 through the conduit 32 to the second end 36 thereof. The pump means 40 comprises a liquid pump as commonly known in the art. The pump 40 may be controlled to selectively draw the sample 12 into the conduit 32 and initially to the infrared spectrometer 18 for testing, and subsequently to the optical emission spectrometer 24.

The assembly 10 may optionally include a heater 42 operatively connected to the conduit 32 for heating the sample 12 of oil prior to being tested. It is desirable to first heat the sample of oil to lower the viscosity thereof to facilitate the transfer of the oil through the conduit 32. The heater 42 is connected about the conduit 32 between the nozzle 38 and the infrared spectrometer 18 to heat the sample 12.

The assembly 10 also includes a computer controller 50 connected to the pump 40, heater 42, the infrared spectrometer 18 and the optical emission spectrometer 24 for controlling the transfer of the sample 12 to the infrared spectrometer 18 and the optical emission spectrometer 24, and for initiating testing to receive and evaluate the first and second test results. The computer controller 50 may be any type of commonly available computer based system with memory for analyzing the results and controlling the remainder of the assembly 10. The computer controller 50 operates under the flow chart of FIGS. 4a and 4b, as subsequently discussed. The computer controller 50 includes a processor 51 and sample memory 52 for storing working parameters, the test results and identification information associated with the sample 12. The computer controller 50 is of the type able to operate in a Windows® format and run the software of the invention coded in Foxpro and Visual Basic in a DOS shell.

The assembly 10 includes a keyboard 54 connected to the computer controller 50 for allowing input of identification information and data of the sample 12 for reception by the computer controller 50. The information is stored in the memory 52 to distinguish the sample 12 and associated test results, from other samples 12. The keyboard 54 also allows editing functions of the identification information, software program, and variables or parameters as commonly known in the art.

The assembly 10 also includes a display screen 56 connected to the computer controller 50 for displaying the input of identification information and the output of the test results, or any other analysis or results provided by the computer controller 50. Such a display screen 56 is commonly known in the art.

The assembly 10 also includes a printer 58 connected to the computer controller 50 for printing test and analysis results. The computer controller 50 may dump the analysis information and any trending or diagnosis onto the printer 58.

The assembly 10 includes a bar code reader 60 connected to the computer controller 50 for reading an identification code from a bar code label 61 on a container 62 holding the sample 12. Each of the containers 62 generally include a different identification code thereon for reading by the bar code reader 60. This code is input into the computer controller 50 and then stored in memory 52 with the sample information input from the key board 54 for a sample 12. Typical bar code readers 60 are commonly known in the art. The identification code may alternatively be input by the operator via the keyboard 54 from the code on the container 62.

The test assembly 10 includes a modem 66 to allow external communication with a remote, central computer 70 which accumulates results from each of the remote test assemblies 10. The central accumulating computer 70 is part of the analyzing system 100, and is located at a remote area to receive information from each of the test assemblies 10. The function of the remote central computer 70 will be subsequently discussed.

A discard container 68 is located below the second end 36 of the conduit 32 to collect the unused portion of the sample 12 of oil which flows out of the optical emission spectrometer 24.

The housing 14 on its exterior of the structure 15 supports the keyboard 54, display screen 56, printer 58, and bar code reader 60 along with the first end 34 of the conduit 32 protruding from the housing 14 with the nozzle 38 extending therefrom. A container holder 64 is positioned beneath the flexible nozzle 38 to receive the container 62 so that the nozzle 38 can be directed and moved into the sample 12 of oil.

Enclosed within the housing 14 on its interior for protection thereof is the infrared spectrometer 18, optical emission spectrometer 24, remainder of the conduit 32, discard container 68, the pump 40, optional heater 42, and the computer controller 50.

Figure 3:
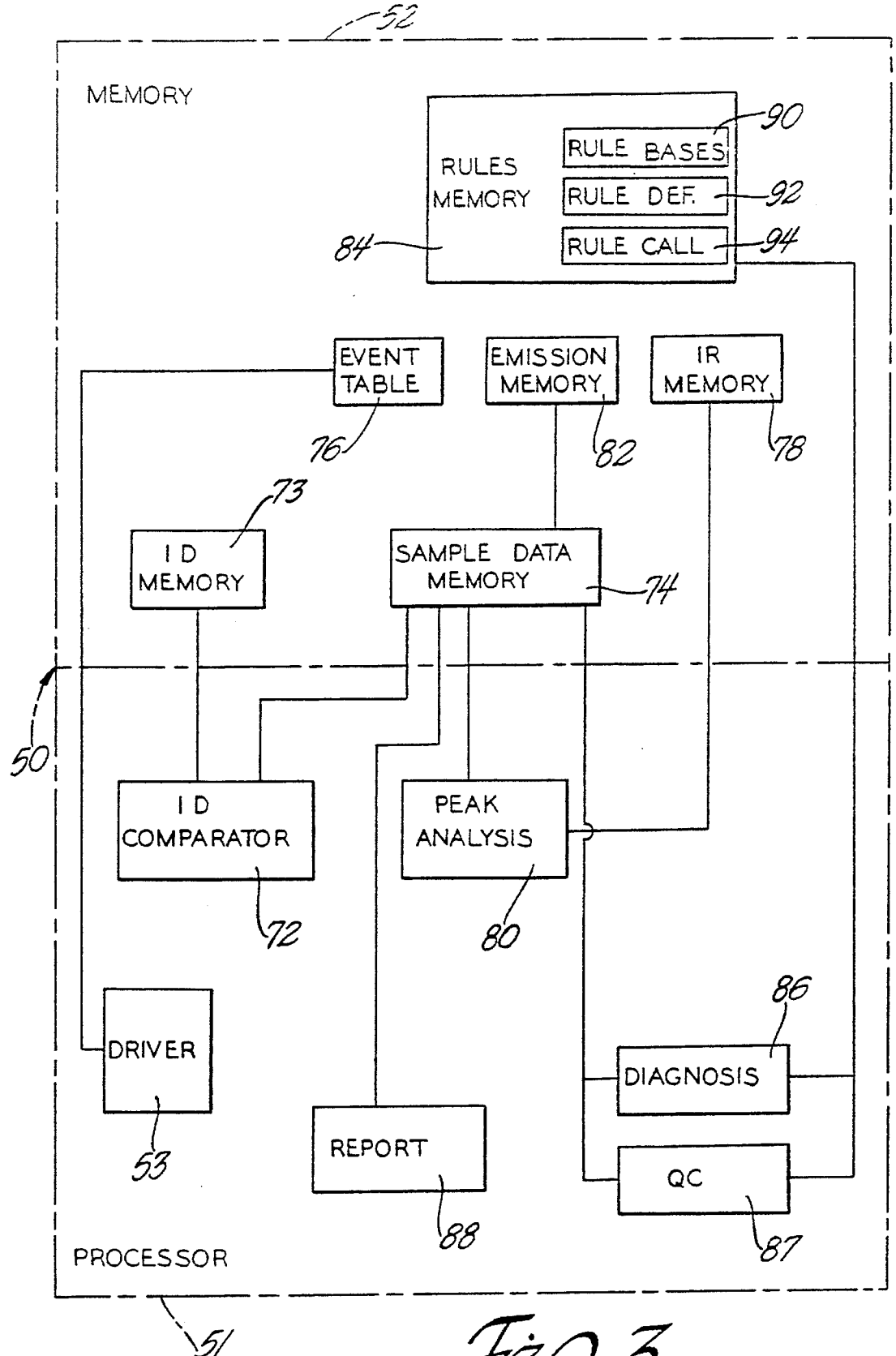
FIG. 3 is a schematic diagram of the computer controller.

The computer controller 50 is schematically illustrated in FIG. 3. The results from the infrared spectrometer 18 includes peak values from the generated spectrum, polled from the infrared spectrometer 18 dynamically by the computer controller 50. The results from the optical emission spectrometer 24 consists of various metal quantities in the samples. This data is passed to the computer controller 50 in the form of a text file. In general, the computer controller 50 controls the infrared spectrometer 18, optical emission spectrometer 24, pump 40, heater 42, display screen 56, printer 58. The computer controller 50 manages and provides the timing for the components.

The controller 50 includes identification memory 73 for storing used identification numbers. The controller includes an identification comparator 72 for receiving the identification code input either by the bar code reader 60 or the keyboard 54 to ensure that the identification number has not been previously utilized and is unique by comparing it to the numbers in the identification memory 70. If the identification number has been utilized, an alert message is displayed on the display screen 56 and the computer controller 50 awaits input of a unique identification number.

The computer controller 50 also includes sample data memory 74 for storing information regarding tested samples. For each sample, the sample data memory 74 includes the information of ("samp_osa"): identification number, assembly number, customer name, unit code, system, unit type, make, model, time units (hours or miles), total time (total time on unit), fluid time (time on oil), fluid type (type of oil), oil brand, oil capacity, oil capacity units, all of which are initially set up for a sample prior to testing. The identification, assembly number, date and time are filled in automatically by the processor 51. The system information may be selected from a check list which includes pump, industrial, gear box, engine-diesel, engine-gasoline, engine-natural gas, turbine, new oil.

Other information which is input into the sample data memory 74 by the processor 51 for each sample includes the following: diagnostic codes, diagnostic text, enter date, enter time, aluminum, chromium, copper, iron, lead, tin, nickel, silver, silicone, sodium, potassium, boron, magnesium, zinc, water, fuel, nitrogen fixation, oxidation, pentane/toluene and solubles and resins, total base number (TBN), total acid number (tan), and viscosity.

Also included is an event table memory 76 for storing information utilized by the controller 50 to control the timing sequence and rates of the pump 40, and the infrared spectrometer 18 and emission spectrometer 24. FIG. 5a is illustrative of an event table which includes the start time and rate information.

IR memory 78 stores the received spectrograph from the infrared spectrometer 18, and includes values and parameters which enables the controller 50 through peak analysis means 80 to determine soot, oxidation, nitration, water and glycol. Such calculations and fourier transform analysis are commonly known which are based on the location of the peak value in the spectrum and the height thereof.

The peak analysis means 80 analyzes the stored spectrograph to obtain "parts per million" values and stores the resultant calculations in the sample data means 74 for the specified sample. Typical values may include the following: glycol equals 4.3, V100C equals 15.8, V40C equals 32.1, V100F equals 32.0, V210F equals 15.7, TAN equals 12, and TBN equals 9.8. The V values indicate viscosity at the indicated temperatures, either in units of C° or F°, which are standard industry measurements.

The controller 50 receives the data from the emission spectrometer 24 as a text file and is received in emission memory 82. The information is then stored with the sample data in the sample data memory 74. Indicative of the emission memory 82 for a specified sample is as follows: AL=75.0, CU=50.4, FE=51.2, PB=321.1, SI=1.15, ZN=2.2, K=456, CR=54.2, and SN=45.1.

The controller 50 also includes a rules memory 84 for comparison with the data in the data sample memory 74 by diagnosis means 86 upon complete testing thereof, to determine condition and diagnosis of the test results. Different rules may be utilized for different types of engines, models, makes, etc. Depending on this type information depends on the rules utilized. Different rules are for diagnosis at a refinery, standard used oil diagnosis, special used oil diagnosis to accommodate unusual climate, standard industrial diagnosis, etc.

The rules memory 84 is partitioned to include a list of rule bases 90, list of rule definitions 92, and rule call table 94. The list of rule bases 90 includes a rule base identification and description. The rules base identification is unique and identifies the system type which is the source of the oil. For example, the table shown in FIG. 5b may be utilized.

The prefix "QSAD" rule bases are utilized for automatic diagnosis, and the "QC" rule bases are utilized to check and verify the data provided by the spectrometers 18, 24, i.e., provides windows of acceptable values.

The list of rule definitions 92 include a rule identification, rule expression and comments. The rule expression is any Foxpro compatible code (or other software system code) that, when evaluated at run-time, returns a Boolean value (true/false). Any fields in the data memory 74 are available for use in the rules. The RR( ) function allows rules to call other rules. Example of typical rules are shown in FIG. 5c.

The rule call table 94 specifies which rule definitions to process for which bases in what order, and what action to take in the event of a "true" rule. The rule base identification identifies one in the list of rules 90 and the rule identification identifies a rule in the list of rule definitions 92. The sequence number indicates the order in which rule calls within a particular rule base are processed, and may be repeated. The custom function CREPLACE includes memory table (test data), key (expression of value to seek on within table to identify proper record), field (in the test data to act on), value (value to add to field), concatenate/overwrite value flag (whether to replace existing contents of table-value or add to existing contents) and append new record if not found flag (whether to append a new record if the seek on key fails). FIG. 5d is exemplary of the rule call table 94.

Figure 4A:
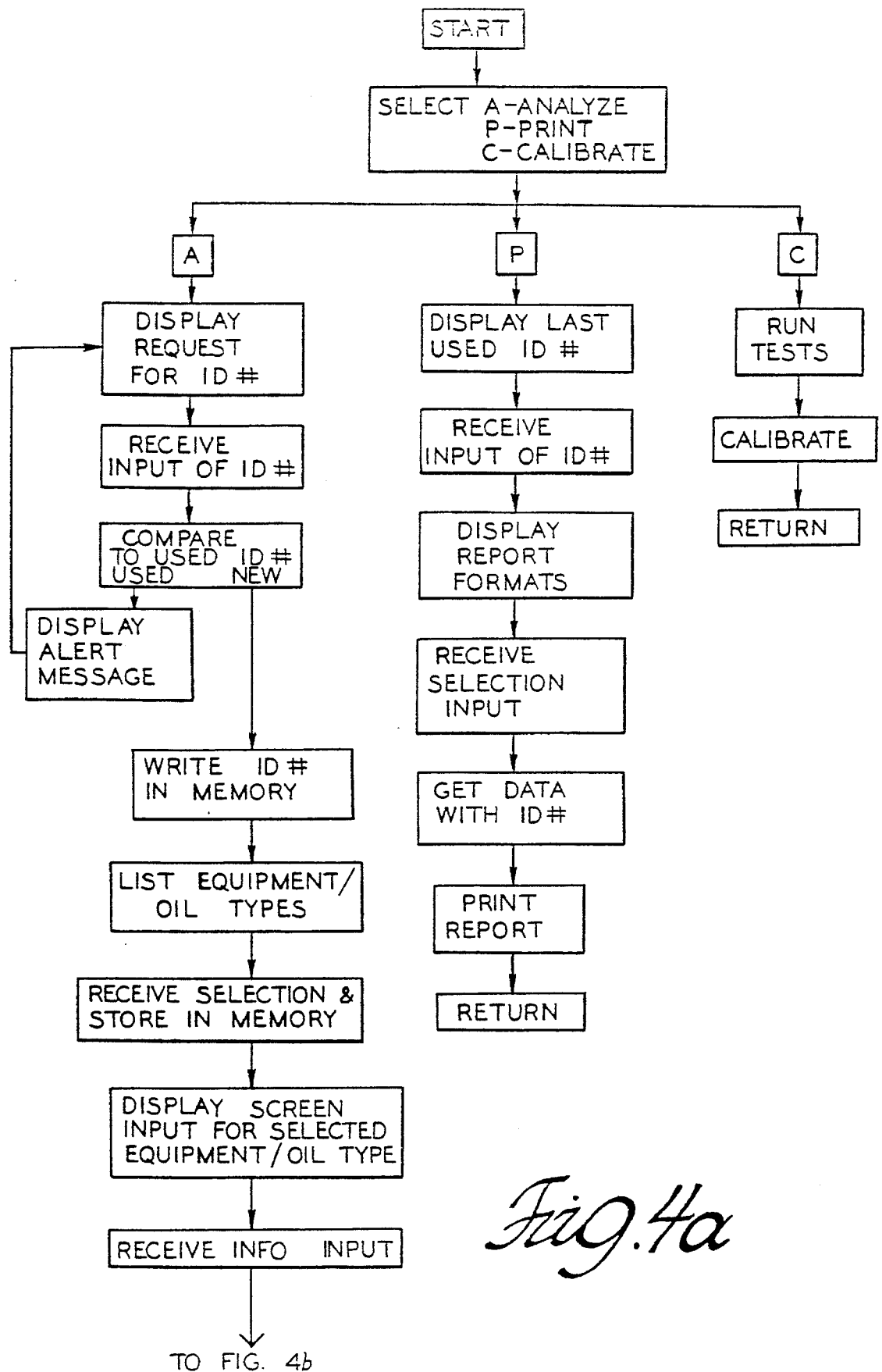
FIGS. 4a and 4b are a flow chart of the operation of the computer controller.
Figure 4B:
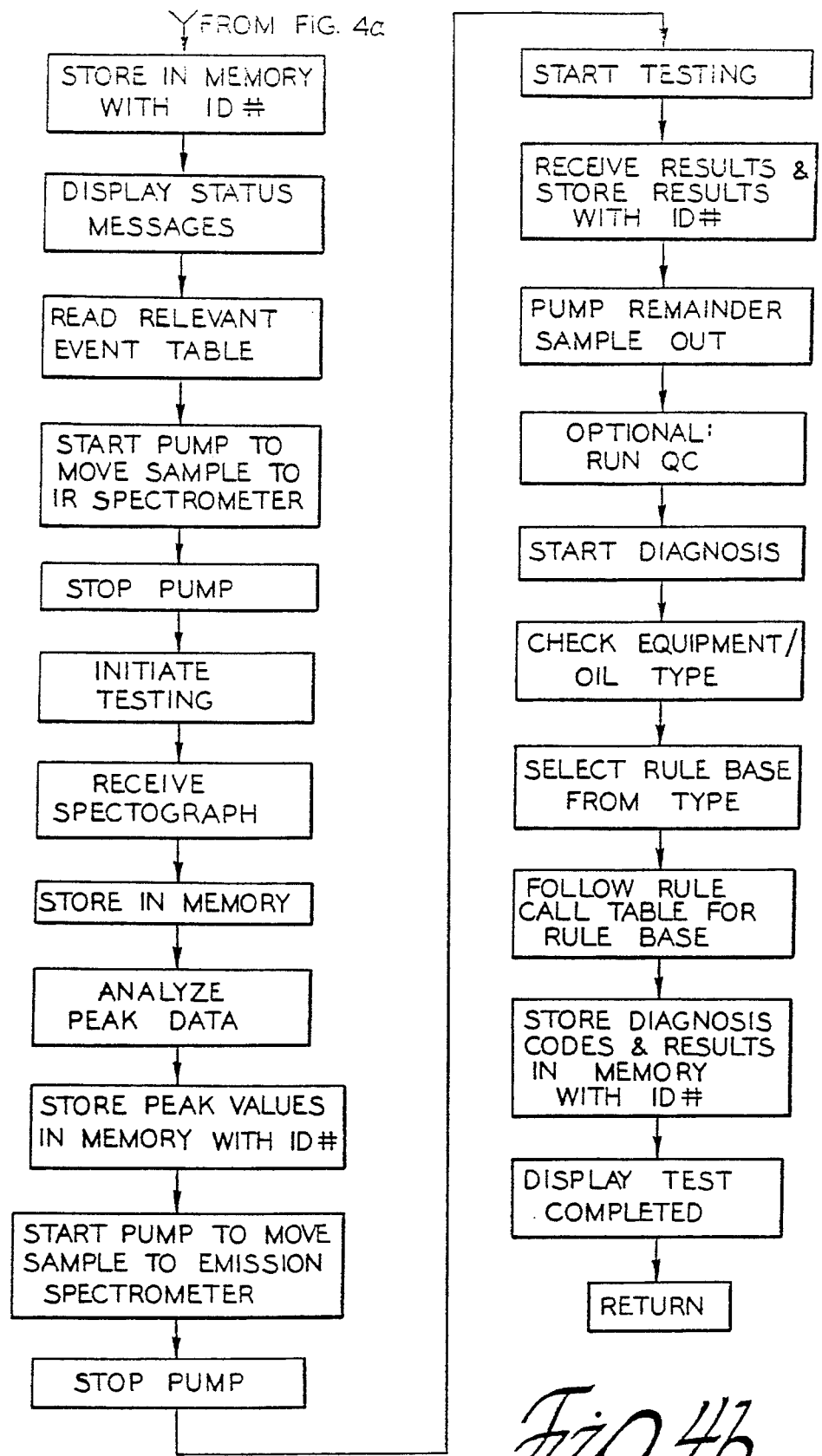

In general, the computer controller 50 operates according to the flow chart illustrated in FIGS. 4a and 4b. The controller 50 first displays the following selections: A-analyze a sample, P-print a report, C-check/calibrate. The "A" selection allows the assembly 10 to automatically test and diagnose a sample, the "P" selection prints the report of resulting diagnosis, and the "C" selection provides automatic calibration of the assembly 10.

If the "A" selection is made, the following occurs. The identification number is input by the operator on the keyboard 54 or by the bar code reader 60. The identification comparator 72 compares the input identification number to the used identification numbers stored in identification memory 73. If the number exists in the memory 73, an alert message is displayed on the screen 56 indicating prior use thereof and unavailability, and the program awaits a new identification number. If the number does not exist in memory 73, the input identification number is written into the memory 73 and the program continues.

Thereafter, the controller 50 requests equipment or unit data which identifies the oil or fluid and source thereof. The controller 50 lists equipment and oil type as follows: pump, industrial, gear box, engine-diesel, engine-gasoline, engine-natural gas, turbine, new oil. Upon selection of one of the former, the controller 50 stores in sample data memory 74 the identification number and selection, and thereafter displays a data entry screen for entry of further data relating to the sample 12. A different data entry screen may be displayed for each different type of equipment/oil type, depending on the data variables desired. This information includes data about the engine and the oil being analyzed so that the test results may be properly categorized and analyzed by the appropriate rule bases. The data provides information to the computer controller 50 for diagnosis and is included on the report for reference. Such information includes the automatic display of identification number, date and time, and requests entry of information of customer name, unit identification, unit make, unit model, time units (hours and miles), total number of units oil in service, total number of units unit in service, oil type, oil brand, gross oil capacity and units thereof. This sample information is stored in the sample data memory 74 with its associated identification number.

Thereafter, the controller 50 displays on the display screen 56 messages of the execution of each test until completion of the test such messages may include: insert nozzle in sample, processing sample, conducting infrared test, conducting emission test, processing results, tests completed.

In order for the controller 50 to automatically test the sample 12, the event table 76 is read for the type of sample based on the equipment/oil type. The table 76 allows the controller 50 through driver means 53 to drive the operation of the pump 40, infrared spectrometer 18, and optical emission spectrometer 24. The timing and sequence of each of these components is specified in this event table 76, as previously illustrated.

The computer controller 50 starts the pump 40 to draw the sample 12 through the nozzle 38 and into the conduit 32. This sample 12 is moved to the flow cell 21 of the infrared spectrometer 18 and is drawn therepast to ensure a clean sample is tested, i.e., no residue from the previous sample. The pump 40 is then stopped. The controller 50 instructs the infrared spectrometer 18 to start testing. The controller 50 awaits to receive the test information from the infrared spectrometer 18, i.e., spectrograph.

The IR spectrograph is received by the controller 50 and stored in the IR memory 78, and then analyzed by peak analysis means 80. The peak analysis means 80 isolates peaks at various locations on the spectrograph and the magnitude thereof to obtain a standardized value for glycol, soot, fuel, water, viscosity, TAN, TBN. The results are stored in the sample data memory 74 with the associated identification number.

The controller 50 reinitates the pump 40 to pump the sample 12 to the optical emission spectrometer 24 based on the event table 76. A specified amount of the sample 12 is pumped through the optical emission spectrometer 24 to ensure a clean sample 12. The controller 50 instructs the electric emission spectrometer 24 to begin testing. Thereafter, the controller 50 waits for the text file to be produced by the optical emission spectrometer 24 and received in emission memory 82. The text file is stored in the sample data memory 74 with the associated identification number.

Thereafter, the controller 50 pumps the remainder of the sample 12 through the conduit 32 to the discard container 68. The test information is stored in memory 52 with the associated identification number and data.

Optionally, the test results are checked by running the appropriate rule base for QC (quality control). The quality means 87 utilizes the QC rules in rules memory 84 to ensure all test results are feasible, and may adjust or modify results if out of acceptable range. An alert message will be indicated if some tests are too inaccurate. For example, a test result may be impossible for the type of oil being tested. This will ensure that the test results are valid and feasible. The QC rule base exists to test each test result value.

Diagnosis of the sample data and test results occurs in the diagnosis means 86 with the rule memory 84. As previously discussed, the sample data is compared to the relevant rules of the rules memory 84, and a numerical and textual diagnosis is developed. The resultant diagnosis codes and text are stored in the sample data memory 74.

The diagnosis means 86 first looks to the equipment and oil type to determine which of the rule bases 90 is to be utilized. The new oil selection could designate the refinery, i.e., USAD-R rule base. The engine selections could designate the standard used oil diagnosis, i.e., USAD-U rule base. Further development of the rule bases may occur based on the equipment type, make, model, etc. However, for purpose of illustration, rules and bases of a generic engine is utilized.

Once the rule base is selected based on the input sample information, the diagnosis means 86 may act on the rule call table 94 to utilize the rules associated with the selected rule base to diagnose the sample 12. The rules and boolean results are determined for each rule and are stored in the diagnostic fields in the data memory 74. The controller 50 indicates to the operator that testing and diagnosis is completed.

When the operator selects "P" to print a report, the controller 50 prompts the operator to input an identification number. The identification number of the most recently analyzed sample 12 appears and can be edited if another number is desired. After the operator confirms the identification number displayed or enters a new one, the controller 50 displays possible forms of reporting, such as a diagnosis report with raw data, or a diagnosis report without raw data. The operator selects one of the types of reports, and the controller 50 gets the data from sample data memory 74 and formats the information in report means 88 and sends same to the printer 58. The report means 88 includes the possible reporting formats such that the data is patterned therein.

With regard to "C" or the check/calibrate section, the controller 50 drives the infrared spectrometer 18 and emission spectrometer 24 according to a selected calibration event scheduled for internal and automatic calibrations of the spectrometers 18, 24.

Wear metals are the key metals worn from the friction surfaces in an oil-lubricated unit. As the unit runs, bacteria-size particles are produced and the oil holds them in suspension. The measurement of these particles in the oil can identify where the wear is occurring. For example, aluminum occurs from pistons, blocks and pumps. Chromium occurs in piston rings, roller-taper bearings, and coolant additives. Copper occurs from bearings, oil cooler, clutches, trust washers and trust plates. Iron occurs from crank shaft, valve train, cylinders, gears and bearings. Lead occurs from bearings, additives in some fuels and oil additives. Tin occurs from bearings and pistons. Nickel occurs from exhaust valves. Silver occurs from bearings and wrist-pin bushings. Silicone may indicate the presence of dirt, which is the most common cause of system wear. It may also be a sealant or an indicator of the presence of a silicone based additive in the lube oil and/or coolant. Sodium is found as an additive in engine coolant, but is frequently used as a lube oil additive. Potassium and boron are also common coolant additives. Additives such as magnesium, molybdenum, calcium, phosphorus, and zinc are ingredients that can be blended into the oil to improve its life and performance. Water and light concentrations can be condensation due to a cold running system. High concentrations may be from cooling system or outside the environmental contamination. Glycol is in the formulation of most commercial anti-freezes and is present indicates a serious coolant leak. Soot is an indication of the build up of dispersed carbon that has occurred due to excessive below-by in the engine. Fuel in the oil indicates faulty combustion, rich air-fuel mixture or poor injection.

All of these materials can be measured by the subject assembly 10, and diagnosed as to potential or future problems caused by these materials depending on the oil system. Quantities may be predetermined for each material to determine when harmful or normal. Such quantities may be accumulated over time from tests on several similar sources. Wear data is also accumulated in this manner to determine the quantities versus wear on the source, i.e., engine.

The remote central computer 70 receives data from each of the test assemblies 10 for evaluation, trending, and reporting. Remote central computer 70 also includes a modem 71 for communication with the modem 66 of the test assembly 10. Information which is transferred from each of the test assemblies 10 includes all data sample information in the sample data memory 74 relating to test results and analysis thereof. This information is accumulated within the central computer 70 and may be analyzed based on geographical location, type of vehicle, make and model, etc., to determine general trending of oil characteristics and wear based on a vast amount of data. This trending and evaluation at the remote central computer 70 incorporates significant amount of result from all the test assemblies 10. Furthermore, the central computer 70 can update the rules 92 or rule bases 90 or rule call 94 in the rules memory 84 at each test assembly 10 through the modems 66, 71 based on the new data or quantity thereof. Any other part of the programming of the controller 50 at the test assembly 10 may be modified from the remote central computer 70.

The remote central computer 70 may provide reporting based on any field in the sample data information and may provide evaluation on any of the fields. Wear pattern data may be analyzed and reported. This allows evaluation and reporting on a vast amount of data collected, to allow analysis based on source or engine type, etc. This can provide data to the manufacturers of general problems or trends in their particular engines, parts, etc.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims wherein reference numerals are merely for convenience and are not to be in any way limiting, the invention may be practiced otherwise than as specifically described.

What is claimed is:

1. An oil analysis system for analyzing the contents of oil, comprising:

a plurality of isolated and remote oil test assemblies (10) each including a liquid conduit (32) for transferring a sample of oil (12) therethrough and having a first end (34) for receiving said sample of oil and a second end (36) for disposing of said sample of oil, a pump (40) operatively connected to said liquid conduit (32) for drawing said sample of oil (12) into said first end (34) and transferring said sample of oil through said liquid conduit, an oil spectrometer (18, 24) connected to said liquid conduit for automatically testing contents of said sample of oil and generating test results data, and a computer controller (50) connected to said pump and said oil spectrometer for automatically controlling the transfer of said sample of oil from said first end to said oil spectrometer and a subsequent transfer of said sample of oil to said second end and for receiving and storing said test results data and associated identification information;

a plurality of modems (66, 71) for transferring said test results data with said associated identification information from said isolated and remote oil test assemblies (10);

a central computer (70) connected to each of said modems (66, 71) for receiving said test results data with said associated identification information from said isolated and remote oil test assemblies and for evaluating said test results data based upon said associated identification information to determine characteristics of said test results data.

2. The oil analysis system according to claim 1 wherein each of said oil spectrometers (18, 24) includes an infrared spectrometer (18) connected intermediate said first end (34) and said second end (36) for non-destructive testing of said sample of oil and generating first test results data and an optical emission spectrometer (24) connected to said second end for destructive testing of said sample of oil and generating second test results data.

3. The oil analysis system according to claim 2 wherein said associated identification information includes information regarding a type of source of said sample of oil and said central computer (70) accumulates and evaluates said first and second test results data from each of said isolated and remote oil test assemblies (10) based on common type of source identification.

4. The oil analysis system according to claim 3 wherein said central computer (70) includes means for determining diagnosis information based on said evaluated first and second test results data and for transferring said diagnosis information to each of said isolated and remote oil test assemblies.

5. The oil analysis system according to claim 4 wherein each of said isolated and remote oil test assemblies (10) include a housing (14) for containing said liquid conduit (32), said pump (40), said infrared spectrometer (18), said optical emission spectrometer (24) and said computer controller (50) as a self-contained and movable unit.

6. The oil analysis system according to claim 5 wherein each of said isolated and remote oil test assemblies (10) includes a keyboard (54) connected to said computer controller (50) and supported by said housing (14) for allowing input of said associated identification information and a display screen (56) connected to said computer controller and supported by said housing for displaying said associated identification information and said first and second test results data, and wherein said computer controller includes a sample memory (52) for storing said associated identification information and said first and second test results data for said sample of oil (12).

7. The oil analysis system according to claim 6 wherein said sample memory (52) includes an event table memory (76) for storing a plurality of event messages indicative of a sequence of events of operation of said pump (40), said infrared spectrometer (18), and said optical emission spectrometer (24).

8. The oil analysis system according to claim 7 wherein said computer controller (50) includes a driver means (53) for automatically operating said pump (40), said infrared spectrometer (18), and said optical emission spectrometer (24) based on said event messages stored in said event table memory (76).

9. The oil analysis system according to claim 8 wherein said sample memory (52) includes a rules memory (84) for storing a rules base table (90) including a list of rule base descriptions associated with different types of sources of oil, and wherein said computer controller (50) includes a diagnosis means (86) for selecting one of said rule base descriptions from said rule base table based upon said sample of oil (12) to be tested and for comparing said first and second test results data with said selected one rule base description for diagnosing said sample of oil.

10. The oil analysis system according to claim 9 wherein said rules base table (90) includes a rule base identification number associated with each said rule base description.

11. The oil analysis system according to claim 10 wherein said rules memory (84) includes a list of rule definitions (92) containing a plurality of rule expressions having predetermined values for diagnosing said sample of oil (12) and associated rule identification numbers.

12. The oil analysis system according to claim 11 wherein said rules memory (84) includes a rule call table (94) containing a plurality of actions each associated with one said rule base identification numbers and one of said rule identification numbers so that upon selection of one of said rule base descriptions for use in diagnoses, selected ones of said rule expressions are automatically associated therewith.

13. An oil analysis system for analyzing the contents of oil, comprising:

a plurality of isolated and remote oil test assemblies (10) each including a liquid conduit (32) for transferring a sample of oil (12) therethrough and having a first end (34) for receiving said sample of oil and a second end (36) for disposing of said sample of oil, a pump (40) operatively connected to said liquid conduit (32) for drawing said sample of oil (12) into said first end (34) and transferring said sample of oil through said liquid conduit, an oil spectrometer (18, 24) connected to said liquid conduit for automatically testing contents of said sample of oil and generating test results data, and a computer controller (50) connected to said pump and said oil spectrometer for automatically controlling the transfer of said sample of oil from said first end to said oil spectrometer and a subsequent transfer of said sample of oil to said second end and for receiving and storing said test results data and associated identification information;

a modems (66, 71) for transferring said test results data with said associated identification information from said plurality of isolated and remote oil test assemblies (10) and for transferring associated characteristics of said samples of oil back to of isolated and remote oil test assemblies; and a central computer (70) connected to each of said modems (66, 71) for receiving said test results data with said associated identification information from said isolated and remote oil test assemblies, for evaluating said test results data based upon said associated identification information to determine said associated characteristics of said test results data and for sending said associated characteristics to said isolated and remote oil test assemblies.

14. The oil analysis system according to claim 13 wherein each of said oil spectrometers (18, 24) includes an infrared spectrometer (18) connected intermediate said first end (34) and said second end (36) for non-destructive testing of said sample of oil and generating first test results data and an optical emission spectrometer (24) connected to said second end for destructive testing of said sample of oil and generating second test results data.

15. The oil analysis system according to claim 14 wherein said associated identification information includes information regarding a type of source of said sample of oil and said central computer (70) accumulates and evaluates said first and second test results data from each of said isolated and remote oil test assemblies (10) based on common type of source identification.

16. The oil analysis system according to claim 14 wherein said computer controller (70) includes an event table memory (76) for storing a plurality of event messages indicative of a sequence of events of operation of said pump (40), said infrared spectrometer (18), and said optical emission spectrometer (24) and a driver means (53) for automatically operating said pump, said infrared spectrometer, and said optical emission spectrometer based on said event messages stored in said event table memory.

* * * * *